United States Patent
Yoon et al.

(10) Patent No.: US 10,314,534 B2
(45) Date of Patent: Jun. 11, 2019

(54) WEARABLE DEVICE ADAPTIVELY CONTROLLABLE BASED ON BIOINFORMATION, SYSTEM INCLUDING THE SAME, AND OPERATING METHOD THEREOF

(71) Applicant: Samsung Electronics Co., Ltd., Suwon-si (KR)

(72) Inventors: Seungkeun Yoon, Seoul (KR); Ui Kun Kwon, Hwaseong-si (KR); Changmok Choi, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 214 days.

(21) Appl. No.: 14/994,356

(22) Filed: Jan. 13, 2016

(65) Prior Publication Data
US 2016/0206239 A1 Jul. 21, 2016

(30) Foreign Application Priority Data

Jan. 19, 2015 (KR) .................. 10-2015-0008847

(51) Int. Cl.
*A61B 5/00* (2006.01)
*G16H 40/63* (2018.01)
(Continued)

(52) U.S. Cl.
CPC .......... *A61B 5/486* (2013.01); *A61B 5/02055* (2013.01); *A61B 5/0488* (2013.01);
(Continued)

(58) Field of Classification Search
CPC ..... A61B 5/6843; A61B 5/6844; A61B 5/681; A61B 5/683; A61B 5/6831; A61B 5/6835; A61B 5/684
See application file for complete search history.

(56) References Cited

U.S. PATENT DOCUMENTS 8,541,745 B2   9/2013  Dickinson et al.
8,721,388 B2   5/2014  Quaranta
(Continued)

FOREIGN PATENT DOCUMENTS

CN   1886090 A   12/2006
CN   104042193 A   9/2014
(Continued)

OTHER PUBLICATIONS

Extended European Search Report dated Jun. 6, 2016 in counter European Application No. 15184150.9 (9 pages, in English).
(Continued)

*Primary Examiner* — Michael W Kahelin
(74) *Attorney, Agent, or Firm* — NSIP Law

(57) ABSTRACT

A electronic device, a system including the wearable electronic device, and an operating method of the wearable electronic device are disclosed. The electronic device includes a biosensor configured to sense bioinformation on a body of a user wearing the electronic device. The electronic device also includes a controller configured to determine a state of the user based on the bioinformation and surrounding environment information of a surrounding environment of the user, and control a change in a function of the electronic device based on the state of the user.

36 Claims, 16 Drawing Sheets

(51) Int. Cl.
*G06F 1/16* (2006.01)
*H04M 1/725* (2006.01)
*A61B 5/0205* (2006.01)
*A61B 5/0488* (2006.01)
*G06F 19/00* (2018.01)
*A61B 5/11* (2006.01)

(52) U.S. Cl.
CPC ............ *A61B 5/681* (2013.01); *A61B 5/7264* (2013.01); *G06F 1/163* (2013.01); *G06F 19/00* (2013.01); *G06F 19/3481* (2013.01); *G16H 40/63* (2018.01); *H04M 1/72569* (2013.01); *A61B 5/0205* (2013.01); *A61B 5/1114* (2013.01); *A61B 5/4809* (2013.01); *A61B 5/6843* (2013.01); *A61B 5/6898* (2013.01); *A61B 2503/10* (2013.01); *A61B 2560/0242* (2013.01); *A61B 2562/0219* (2013.01); *H04M 2250/12* (2013.01)

(56) References Cited

U.S. PATENT DOCUMENTS

| | | |
|---|---|---|
| 2002/0083025 A1 | 6/2002 | Robarts et al. |
| 2008/0194917 A1 | 8/2008 | Muehlsteff et al. |
| 2009/0051544 A1* | 2/2009 | Niknejad ............... G06F 3/011 340/573.1 |
| 2009/0203972 A1* | 8/2009 | Heneghan ............ A61B 5/0507 600/301 |
| 2009/0306485 A1 | 12/2009 | Bell |
| 2013/0194066 A1 | 8/2013 | Rahman et al. |
| 2017/0119314 A1* | 5/2017 | Just ...................... A61B 5/6838 |

FOREIGN PATENT DOCUMENTS

| | | |
|---|---|---|
| CN | 203930836 U | 11/2014 |
| CN | 204044660 U | 12/2014 |
| EP | 1 609 413 A1 | 12/2005 |
| JP | 4430934 B2 | 3/2010 |
| JP | 5281113 B2 | 9/2013 |
| KR | 10-0615446 B1 | 8/2006 |
| KR | 10-2013-0111713 A | 10/2013 |
| KR | 10-1362833 B1 | 2/2014 |
| KR | 10-1384761 B1 | 4/2014 |
| KR | 10-2014-0058502 A | 5/2014 |
| KR | 10-2014-0062890 A | 5/2014 |
| WO | WO 2005/051184 A1 | 6/2005 |
| WO | WO 2007/040878 A1 | 4/2007 |
| WO | WO 2012/170366 A1 | 12/2012 |

OTHER PUBLICATIONS

Chinese Office Action dated Oct. 19, 2018 in corrresponding Chinese Patent Applicatino No. 201511017451.7 (26 pages in English, 18 pages in Chinese).

* cited by examiner

10

1200

WEARABLE DEVICE ADAPTIVELY CONTROLLABLE BASED ON BIOINFORMATION, SYSTEM INCLUDING THE SAME, AND OPERATING METHOD THEREOF

CROSS-REFERENCE TO RELATED APPLICATION

This application claims the benefit under 35 USC 119(a) of Korean Patent Application No. 10-2015-0008847, filed on Jan. 19, 2015, in the Korean Intellectual Property Office, the entire disclosure of which is incorporated herein by reference for all purposes.

BACKGROUND

1. Field

The following description relates to a wearable electronic device, a system including the wearable electronic device, and an operating method of the wearable electronic device.

2. Description of Related Art

Various mobile devices have been developed amid a proliferation of smartphones. Such mobile devices provide convenience to people living in modern times. A growing computing power of the mobile devices enable users to perform numerous tasks, typically performed using, for example, a personal computer (PC).

Recently, wearable mobile devices have been introduced. A wearable mobile device receives information obtained by a smartphone through a wireless data network.

Such a wearable mobile device may not be deformed or adjusted onto a user for comfort, usability, and practicality, once the wearable mobile device is suitably worn on a body of a user.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In accordance with an embodiment, there is provided an electronic device, including a biosensor configured to sense bioinformation on a body of a user wearing the electronic device; and a controller configured to determine a state of the user based on the bioinformation and surrounding environment information of a surrounding environment of the user, and control a change in a function of the electronic device based on the state of the user.

The controller may be configured to determine the state of the user based on the surrounding environment information and at least one of biosignal information and biosignal measurement information comprised in the bioinformation.

The biosignal measurement information may include an input request from the user to measure a biosignal of the user.

The controller may be configured to determine an exercising state of the user based on the bioinformation and motion information comprised in the surrounding environment information and control the change in the function of the electronic device based on the determined exercising state of the user.

The controller may be configured to determine a stable state of the user based on the surrounding environment information and bio-reaction information comprised in the bioinformation and control the change in the function of the electronic device based on the determined stable state of the user.

The controller may be configured to determine a biosignal measurement state of the user based on the surrounding environment information and biosignal measurement information comprised in the bioinformation and control the change in the function of the electronic device based on the determined biosignal measurement state of the user.

The electronic device may also include an environmental sensor configured to sense the surrounding environment information.

The surrounding environment information may be received from another electronic device communicating with the electronic device.

The biosensor may be configured to generate a sensing signal in response to an input from the user, and the controller may be configured to determine the state of the user in response to the sensing signal, and control the change in the function of the electronic device based on the determined state of the user.

The state of the user may be a biosignal measurement state of the user.

The controller may be configured to control a deformation of a region of the electronic device worn on a portion of a body of the user.

The controller may be configured to control a deformation using an electrode comprised in the biosensor.

The controller may be configured to control the deformation using the electrode through an electroactive polymer (EAP).

The controller may also include a determiner configured to determine the state of the user through a classifier using the surrounding environment information and the bioinformation.

The controller may further include a trainer configured to collect feedback information on the changed function of the electronic device, and train the classifier based on the feedback information, the surrounding environment information, and the bioinformation.

In accordance with an embodiment, there is provided a method of an electronic device, including: sensing bioinformation from a user wearing the electronic device; determining a state of the user based on the bioinformation and surrounding environment information of a surrounding environment of the user; and controlling a change in a function of the electronic device based on the state of the user.

The determining may include determining the state of the user based on the surrounding environment information and at least one of biosignal information and biosignal measurement information comprised in the bioinformation.

The biosignal measurement information may include an input request from the user to measure a biosignal of the user.

The method may also include sensing the surrounding environment information.

The surrounding environment information may be received from another electronic device communicating with the electronic device.

The determining may include determining an exercising state of the user based on the bioinformation and motion information comprised in the surrounding environment information.

The determining may include determining a stable state of the user based on the surrounding environment information and bio-reaction information comprised in the bioinformation.

The determining may include determining a biosignal measurement state of the user based on the surrounding environment information and biosignal measurement information comprised in the bioinformation.

The controlling may include controlling a deformation of a region of the electronic device to be worn on a portion of a body of the user.

The controlling may include controlling a deformation using an electrode comprised in a sensor configured to sense the bioinformation.

The electrode may be deformed through an electroactive polymer (EAP).

The determining may include determining the state of the user through a classifier using the surrounding environment information and the bioinformation.

The method may also include collecting feedback information on the changed function of the electronic device; and training the classifier based on the feedback information, the surrounding environment information, and the bioinformation.

In accordance with an embodiment, there is provided an apparatus, including: a sensor configured to sense bioinformation and information of a surrounding environment of a user wearing an electronic device; and a controller configured to determine a state of the user based on the bioinformation and the surrounding environment information and control a deformation function of a wearable region of the electronic device based on the state of the user.

The surrounding environment information may include at least one of light information, temperature information, noise information, force information, and motion information.

The bioinformation may include at least one of a pulse wave, a skin temperature, a brainwave, a facial muscle movement, and a face temperature.

The controller may include a determiner configured to determine the state as an exercising state or a stable state of the user through a classifier based on the bioinformation and motion information included in the surrounding environment information, and a trainer configured to collect feedback information on the deformation function of the electronic device, and train the classifier based on the feedback information, the surrounding environment information, and the bioinformation.

The determiner may produce data included in the surrounding environment information and the bioinformation as a vector comprising a numerical value of the each data, and use personal information of the user to adjust the state of the user wearing the electronic device, wherein the data comprises acceleration data, coordinate data, and heart rate data, and the personal information comprises an age, a height, and a weight of the user.

In response to the determiner determining that the state of the user is a stable state comprising a sleeping state or a resting state, the controller may control the deformation function of the wearable region worn on a portion of a body of the user by loosening the wearable region.

The controller may execute a function to monitor and record at least one of a resting time and a sleeping time, saturation of partial pressure oxygen ($SpO_2$), save power of the electronic device, music, and a ringtone or vibration mode.

In response to the determiner determining that the state of the user is an exercise state, the controller may control the deformation function of the wearable region worn on a portion of a body of the user by tightening the wearable region.

The control processor may execute a function to monitor and record at least one of an exercise time, a heart rate, an electromyogram (EMG), music, coaching an exercise, and a ringtone or vibration mode.

In response to the determiner determining that the user is measuring a biosignal, the controller may control the deformation function to enable an electrode included in the sensor to be in close contact with skin of the user.

Other features and aspects will be apparent from the following detailed description, the drawings, and the claims.

BRIEF DESCRIPTION OF THE DRAWINGS

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Figure 1:
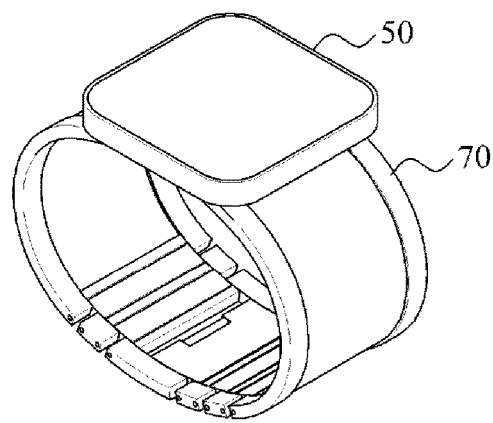
FIG. 1 is a diagram illustrating an example of an electronic device, in accordance with an embodiment.

FIG. 1 is a diagram illustrating an example of an electronic device 10, in accordance with an embodiment.

Referring to FIG. 1, the electronic device 10 includes a main body 50 and a wearable region 70.

The electronic device 10 is a wearable device that a user wears or is suitable for wearing. As one embodiment, the electronic device 10 is illustrated as a watch. However, the electronic device 10 may be configured as another electronic device such as a bracelet, ring, pendant on a necklace, part of a garment, or eye-glasses as the watch is provided only as an illustrative example and, thus, the electronic device 10 may not be limited thereto.

The electronic device 10 is provided in a form of a portable device.

The portable device includes a laptop computer, a mobile phone, a smartphone, a tablet personal computer (PC), a mobile Internet device (MID), a personal digital assistant (PDA), an enterprise digital assistant (EDA), a digital still camera, a digital video camera, a portable multimedia player (PMP), a personal or portable navigation device (PND), a handheld game console, an e-book, or a smart device. The smart device is provided in a form of a smart watch or a smart band.

The main body 50 is a portion distinguishable from the wearable region 70, and includes electronic components that perform overall control on the electronic device 10. The main body 50 includes a display. For example, the display displays a result of monitoring the user wearing the electronic device 10. In one embodiment, the display is provided in a form of a liquid crystal display (LCD). Alternatively, the display is provided in a form of a touch screen, a thin-film transistor liquid-crystal display (TFT-LCD), a light emitting diode (LED) display, an organic LED (OLED) display, an active matrix OLED (AMOLED) display, or a flexible display.

The wearable region 70 is provided to allow the electronic device 10 to be worn on a portion of a body of the user. The portion of the body is, for example, a wrist, a forearm, a face, a neck, an ankle, eyes, and a knee. The wearable region 70 is provided in a form of a band to be attachable to, wearable on, or detachable from the portion of the body of the user.

For example, the wearable region 70 surrounds the portion of the body to be attached. Thus, the electronic device 10 makes direct contact with the portion of the body of the user wearing the electronic device 10 through the wearable region 70. In an alternative configuration, the electronic device 10 makes direct contact with the entire portion of the body of the user wearing the electronic device 10, through the wearable region 70.

The wearable region 70 is provided as an integral part of the main body 50 or is provided to be removable from the main body 50.

Figure 2:
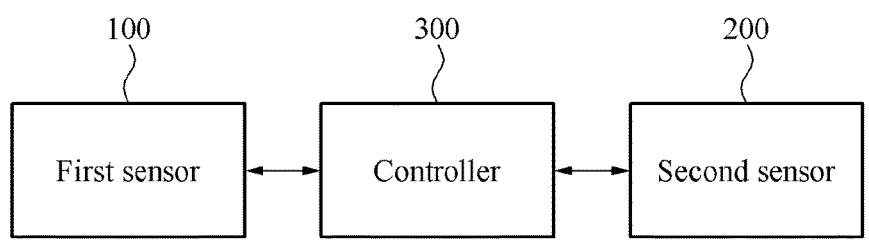
FIG. 2 is a diagram illustrating a configuration of an example of the electronic device of FIG. 1, in accordance with an embodiment.
Figure 3:
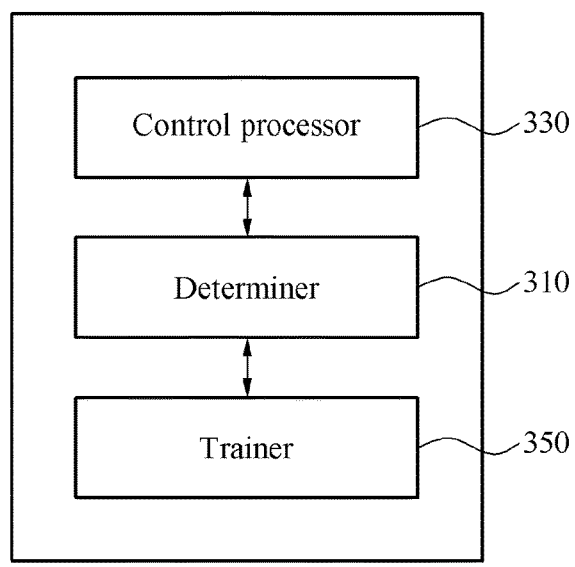
FIG. 3 is a diagram illustrating a configuration of a controller of FIG. 2, in accordance with an embodiment.

FIG. 2 is a diagram illustrating a configuration of the electronic device 10 illustrated in FIG. 1, and FIG. 3 is a diagram illustrating a configuration of a controller 300 of FIG. 2, in accordance with an embodiment.

Referring to FIGS. 1 through 3, the electronic device 10 includes a first sensor 100, a second sensor 200, and the controller 300. The first sensor 100 and the second sensor 200 sense information on a state of a target to be measured, for example, a physical quantity and a chemical quantity.

The first sensor 100 senses surrounding environment information. The surrounding environment information is information associated with an environment, influences, or conditions surrounding a user wearing the electronic device 10 and includes at least one of light information, temperature information, noise information, force information, and motion information. The first sensor 100 senses the surrounding environment information on the surrounding environment of the user including, for example, light, a temperature, noise, a force, a call state, and a motion. For example, the first sensor 100 senses a motion of the user wearing the electronic device 10 and generates the surrounding environment information including motion information of the user. The first sensor 100 may be an environmental sensor.

The motion information includes at least one of an acceleration signal, a rotational signal, a directional signal, and a coordinate signal associated with the motion performed by the user wearing the electronic device 10.

The first sensor 100 includes at least one sensor. For example, the first sensor 100 includes at least one of an acceleration sensor, a gyrosensor, a geomagnetic sensor, and a global positioning system (GPS) sensor.

In one example, in a case of the first sensor 100 including the acceleration sensor, the first sensor 100 generates the surrounding environment information including the acceleration signal based on the movements of the user wearing the electronic device 10.

In another example, in a case of the first sensor 100 including the gyrosensor, the first sensor 100 generates the surrounding environment information including the rotational signal associated with the motion performed by the user wearing the electronic device 10.

For still another example, in a case of the first sensor 100 including the geomagnetic sensor, the first sensor 100 generates the surrounding environment information including a directional signal associated with the motion performed by the user wearing the electronic device 10.

For yet another example, in a case of the first sensor 100 including a global positioning system (GPS) sensor, the first sensor 100 may generate the surrounding environment information including the coordinate signal associated with the motion performed by the user wearing the electronic device 10.

The first sensor 100 outputs the surrounding environment information to the controller 300.

For ease of description, an example in which the surrounding environment information includes the motion information of the user is illustrated. However, the surrounding environment information may include additional information such as light, a temperature, a call state, or a force as an element of the surrounding environment of the user.

The second sensor 200 senses bioinformation of the user wearing the electronic device 10. For example, the bioinformation is information associated with a biosignal of the user wearing the electronic device 10. The second sensor 200 is a biosensor. The bioinformation includes at least one of biosignal information and biosignal measurement information associated with measuring a biosignal.

The second sensor 200 senses the biosignal of the user wearing the electronic device 10 and generates the biosignal information.

A biosignal is indicative of all types of a signal that is measured, monitored, or sensed from a biological being, continually, intermittently, or one time, and a unique signal for each biological being. For example, a biosignal includes an electrocardiogram (ECG) signal, a photoplethysmogram (PPG) signal, an electromyogram (EMG) signal, a voice, and an impedance signal generated from a body.

The second sensor 200 includes at least one sensor. For example, in a case of the second sensor 200 including an EMG sensor, the second sensor 200 generates the bioinformation including an EMG signal of the user wearing the electronic device 10. The EMG signal is a signal generated by muscular contraction or relaxation of a portion of the body of the user on which the electronic device 10 is worn. For example, in a case of the portion being a wrist, the second sensor 200 generates the bioinformation including an EMG signal generated by muscular contraction or relaxation of the wrist.

For example, an EMG signal includes a bioelectric or a biomagnetic signal, a bio-impedance signal, and a biomechanical signal generated in association with a muscle of the portion of the body of the user on which the electronic device 10 is worn. In addition, the EMG signal further includes a light signal passing through the muscle of the portion of the body on which the electronic device 10 is worn and a signal, such as a force, generated by the muscle of the portion of the body. The EMG sensor includes, for example, a photosensor, a piezoelectric sensor, and a force sensor.

The biosignal information includes bio-reaction information on a biological reaction of the user.

For example, a bio-reaction includes a pulse wave, a skin temperature, a brainwave, a facial muscle movement, and a facial temperature.

The bio-reaction information includes stability information of the user wearing the electronic device 10. For example, the stability information is information about a stable state or a resting state of the user wearing the electronic device 10.

In one illustrative example, the second sensor 200 includes at least one of a three channel autonomic nervous system (ANS) sensor, a brainwave sensor, and a capturing sensor.

For example, the three channel ANS sensor senses a heart rate (HR), a heart rate variability (HRV), a peripheral plethysmogram (PPG), a galvanic skin response (GSR), and a skin temperature. The brainwave sensor senses a four channel central nervous system (CNS), and senses a theta wave, an alpha wave, and a beta wave based on a frequency range. The capturing sensor senses a change in a facial expression, a change in a facial muscle, or a behavioral response of the user wearing the electronic device 10.

The second sensor 200 outputs the biosignal information to the controller 300.

In another example, the second sensor 200 senses the biosignal measurement information from the user wearing the electronic device 10. For example, the biosignal measurement information includes an input signal from the user wearing the electronic device 10 to measure a biosignal. The second sensor 200 senses the input signal from the user wearing the electronic device 10 to measure the biosignal. In one example, the user inputs the input signal to initiate measuring of a biosignal. The second sensor 200 functions as an input interface to sense and receive the input signal. Alternatively, the input interface is configured as a separate sensor to sense and receive the input signal.

The second sensor 200 outputs the biosignal measurement information to the controller 300.

Although the first and the second sensors 100 and 200 are illustrated in FIG. 1 as separate sensors, a person of ordinary skill in the relevant art will appreciate that both sensors may be a single structural sensor configured to sense the surrounding environment information of the user and the bioinformation of the user wearing the electronic device 10.

The controller 300 determines a state of the user wearing the electronic device 10 based on the surrounding environment information transmitted from the first sensor 100 and the bioinformation transmitted from the second sensor 200, and controls a change in a function of the electronic device 10 based on the determined state of the user. For example, the state of the user includes various conditions or states in which the user may be placed, for example, exercising, resting, viewing a movie, getting stressed, reading, calling, and driving while drowsy.

Referring to FIG. 3, the controller 300 includes a determiner 310, a control processor 330, and a trainer 350, in accordance with an embodiment.

The determiner 310 determines the state of the user wearing the electronic device 10 through a classifier based on the surrounding environment information and the bioinformation. In one example, the classifier is a state recognition function.

The determiner 310 determines the state of the user based on the surrounding environment information and at least one of the biosignal information and the biosignal measurement information included in the bioinformation. The surrounding environment information includes at least one of light information, temperature information, noise information, force information, and motion information. The bioinformation includes at least one of the biosignal information and the biosignal measurement information of a biosignal.

In one example, the determiner 310 determines an exercising state of the user based on the bioinformation and the motion information included in the surrounding environment information.

In another example, the determiner 310 determines a stable state of the user, for example, a stressful state and a sleeping state, based on the surrounding environment information and the bioinformation. Here, the bioinformation includes the biosignal information, for example, the bio-reaction information.

In still another example, the determiner 310 determines a biosignal measurement state of the user, for example, a state in which a biosignal of the user is being measured and a state in which a biosignal of the user is to be measured, based on the surrounding environment information and the bioinformation.

The determiner 310 produces each set of data or a signal included in the surrounding environment information and the bioinformation as a vector, for example, a numerical value of each set of data, for example, acceleration data, coordinate data, and heart rate data, and substitutes the vector for the classifier.

Figure 4:
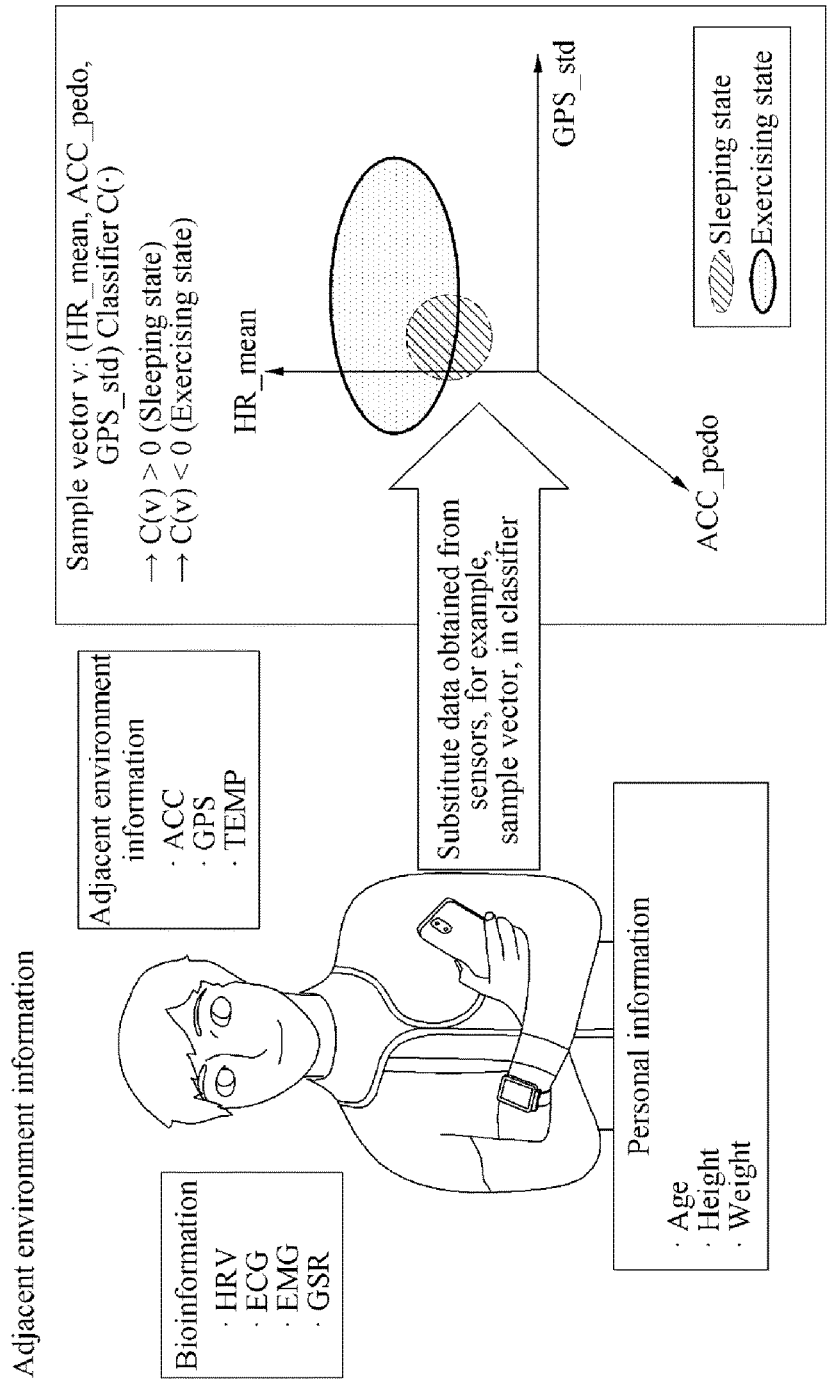
FIG. 4 illustrates an example of an operation to determine a state of a user through a classifier by the determiner of FIG. 3, in accordance with an embodiment.

FIG. 4 illustrates an example of an operation of determining a state of a user through a classifier by the determiner 310 of FIG. 3, in accordance with an embodiment.

For ease of description, as illustrated in FIG. 4, surrounding environment information includes acceleration data (ACC_pedo) and coordinate data (GPS_std), and bioinformation includes heart rate data (HR_mean). However, a person of ordinary skill in the relevant art will appreciate that the surrounding environment information may include more or different data information as previously described with respect to FIGS. 2 and 3.

Referring to FIG. 4, a vector (v) including a numerical value of each set of the data, for example, the acceleration data, the coordinate data, and the heart rate data, is indicated at a position through a classifier (C). The determiner 310 determines the state of the user wearing the electronic device 10 of FIG. 2, for example, a sedentary state, an exercising state, and a sleeping state, based on the position at which the vector is indicated through the classifier.

In addition, the determiner 310 further uses personal information of the user, for example, an age, a height, and a weight of the user, to further determine the state of the user wearing the electronic device 10. For instance, based on predefined reference data associated with age, gender, and medical history, the determiner 310 adjusts the current state of the electronic device 10 by considering the personal information of the user. Thus, the determiner 310 determines a current state of the user more accurately.

The control processor 330, which is also referred to as a structural controller, changes a function of the electronic device 10 based on the state of the user determined by the determiner 310. For example, the function includes an external environment function, for example, a shape of the electronic device 10, and an internal environment function, for example, an internal function setting and an application.

The control processor 330 changes the external environment function of the electronic device 10, for example, the shape of the electronic device 10, based on the state of the user. For example, the control processor 330 changes a shape of the wearable region 70 of the electronic device 10 of FIG. 1 while worn on a portion of a body of the user. In addition, the control processor 330 changes a shape of an electrode included in the second sensor 200 of FIG. 2.

The control processor 330 controls the internal environment function of the electronic device 10. For example, the control processor 330 changes the internal function settings and changes or executes various applications.

For example, in a case of the determiner 310 determining that the user is in a stable state, for example, a sleeping state and a resting state or a sedentary state, the control processor 330 controls a change in the shape of the wearable region 70 of the electronic device 10 worn on the portion of the body of the user. For instance, the control processor 330 controls the wearable region 70 to be further loosened. Thus, the electronic device 10 provides a more comfortable wearing feeling to the user currently being in the stable state. In addition, the control processor 330 changes or executes a function or an application corresponding to recording a stable time, for example, a resting time and a sleeping time, monitoring saturation of partial pressure oxygen ($SpO_2$), saving power of the electronic device 10, selecting music, and/or a ringtone or vibration mode.

For another example, in a case of the determiner 310 determining that the user exercises, the control processor 330 controls and changes the shape of the wearable region 70 to allow the electronic device 10 to be worn on the portion of the body of the user. The control processor 330 controls the shape of the wearable region 70 to be further tightened. Thus, the electronic device 10 is suitably fixed to the portion of the body of the user on which the electronic device 10 is worn and not to be shaken and, as a result, does not hinder the user while exercising. In addition, the control processor 330 changes or executes a function or an application corresponding to recording an exercise time, monitoring a heart rate, measuring an EMG, selecting music, coaching an exercise, and/or a ringtone or vibration mode.

For still another example, in a case of the determiner 310 determining that the user is measuring a biosignal, the control processor 330 controls a deformation to allow an electrode included in the second sensor 200 to be in close contact with skin. Thus, the electronic device 10 more readily measures the biosignal and has an increased accuracy in the measuring. In addition, the control processor 330 changes or executes a function or an application corresponding to recording a biosignal measurement state, a result of the measuring, measuring another biosignal, selecting music, warning of danger, and/or a ringtone or vibration mode.

The user wearing the electronic device 10 may re-change or re-adjust the controlled or changed function of the electronic device 10 based on user convenience or comfort.

The trainer 350 collects feedback information from the changed function of the electronic device 10 and trains the classifier of the determiner 310 based on the feedback information, the surrounding environment information, and the bioinformation. For example, the trainer 350 corrects the classifier of the determiner 310, for example, a state recognition function. In one example, the feedback information includes information on the function of the electronic device 10 controlled to be changed through the controlling of the control processor 330 and information on the changing or adjusting of the function of the electronic device 10 based on the user convenience.

Figure 5:
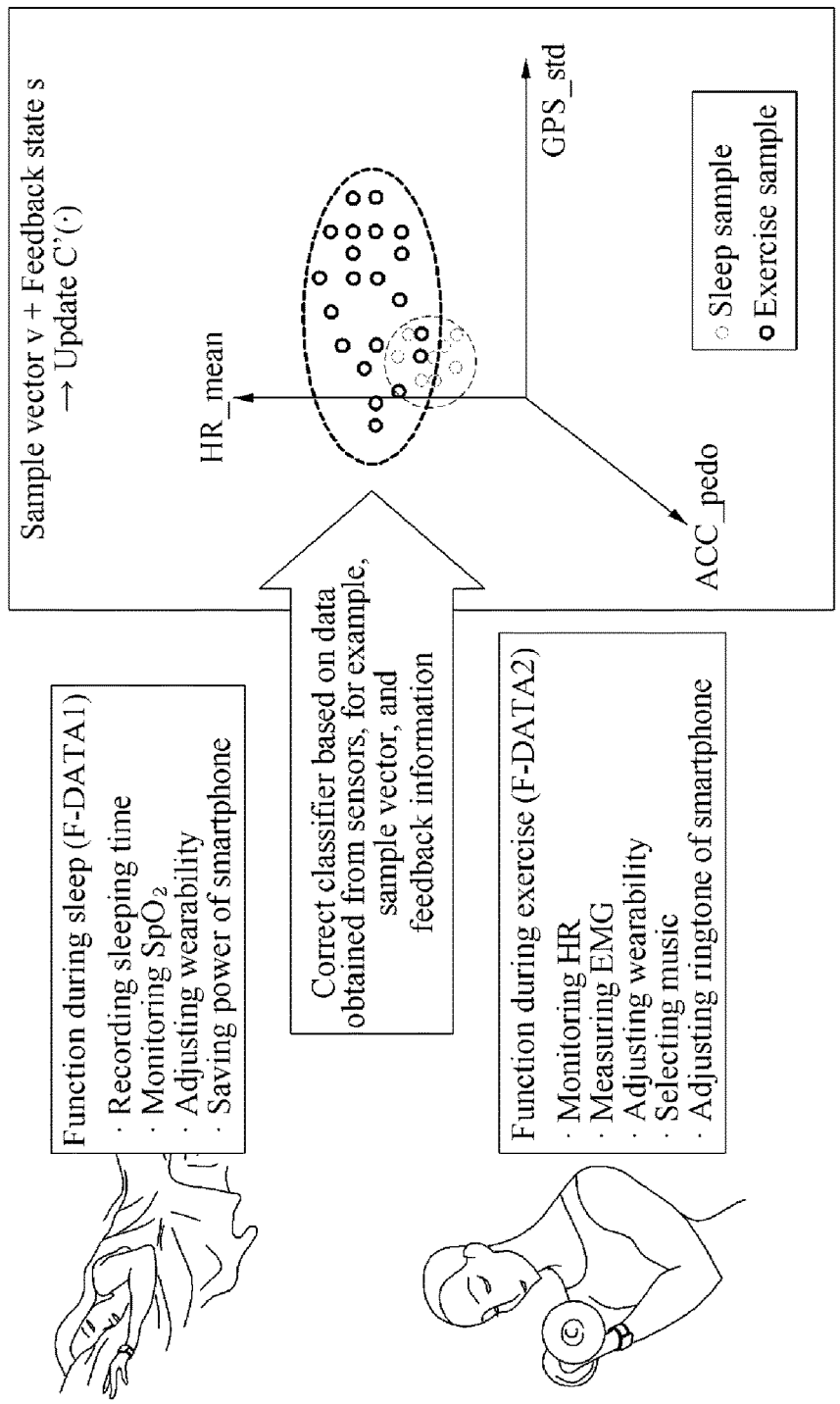
FIG. 5 illustrates an example of an operation of training a classifier using a trainer of FIG. 3, in accordance with an embodiment.

FIG. 5 illustrates an example of an operation of training the classifier by the trainer 350 of FIG. 3, in accordance with an embodiment.

For ease of description, the example of FIG. 5 illustrates that the trainer 350 collects feedback information associated with a sleeping state and an exercising state of a user. However, a person of ordinary skill in the relevant art will appreciate that the trainer 350 may collect other types of feedback information associated with various activities of the user such as, while at home, the trainer 350 would collect feedback information associated with housework activities, or while at work, the trainer 350 would collect feedback information associated with the user at his or her desk or amount of walking during work hours.

Referring to FIG. 5, the trainer 350 corrects the classifier, for example, a state recognition function, based on feedback information (F-DATA1 and F-DATA2), surrounding environment information transmitted from the first sensor 100 of FIG. 2, and bioinformation transmitted from the second sensor 200 of FIG. 2. As illustrated in FIG. 5, such information is reflected in each sample, for example, a sleep sample and an exercise sample.

Figure 6:
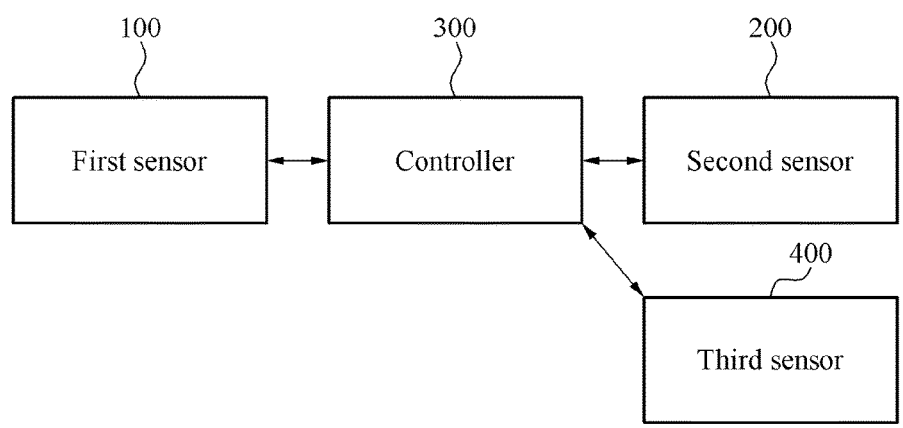
FIG. 6 is a diagram illustrating a configuration of another example of the electronic device of FIG. 1.
Figure 7:
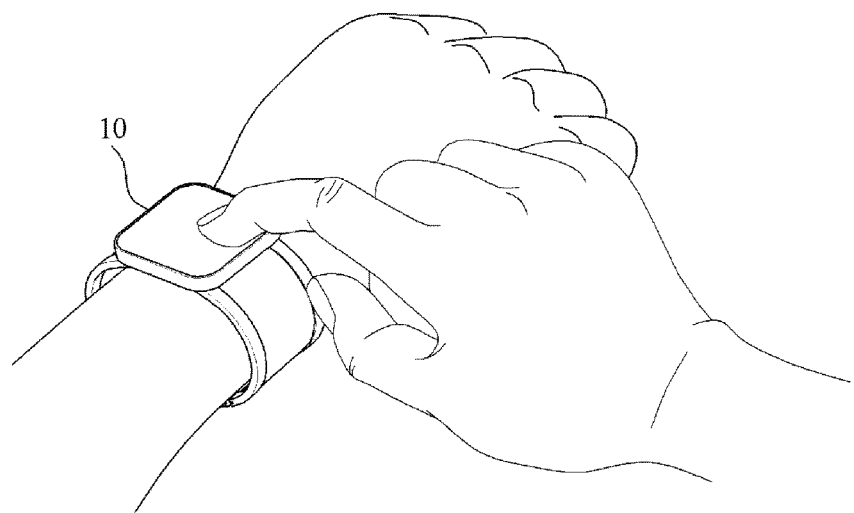
FIG. 7 illustrates an example of an input from the user to control an operation of the electronic device of FIG. 1, in accordance with an embodiment.

FIG. 6 is a diagram illustrating a configuration of another example of the electronic device 10 illustrated in FIG. 1, and FIG. 7 illustrates an example of an input from a user to control an operation of the electronic device 10 of FIG. 1, in accordance with an embodiment.

Referring to FIGS. 1 and 3 through 7, the electronic device 10 includes a first sensor 100, a second sensor 200, a controller 300, and a third sensor 400. The electronic device 10 is provided as a modified configuration of the electronic device 10 illustrated in FIG. 1.

The third sensor 400 detects an input from a user to measure a biosignal of the user wearing the electronic device 10. The third sensor 400 generates a sensing signal in response to the input from the user. The input from the user is a request to initiate measuring of the biosignal. The third sensor 400 may function as an input interface to sense and receive the input from the user. The user wearing the electronic device 10 may input the request through a touch or soft or hard pushbutton.

The third sensor 400 may be separately configured as illustrated in FIG. 6. In an alternative configuration, the third sensor 400 may be included in the first sensor 100, the second sensor 200, or the controller 300.

The controller 300 determines a state of the user in response to the sensing signal output from the third sensor 400, and controls a deformation of the electronic device 10 based on the determined state of the user. For example, the state of the user may be a biosignal measurement state in which the user is either sleeping or exercising.

Configurations and operations of the first sensor 100, the second sensor 200, and the controller 300 illustrated in FIG. 6 may be substantially identical to those of the first sensor 100, the second sensor 200, and the controller 300 illustrated in FIGS. 2 and 3.

Referring to FIGS. 1 through 7, the electronic device 10 provides a high level of convenience to the user wearing the electronic device 10 by recognizing various actions or movements performed by the user, determining a state of the user, and automatically controlling a change in a function of the electronic device 10 based on the determined state of the user.

Furthermore, although in FIGS. 1 through 7 the first and the second sensors 100 and 200 are illustrated as separate sensors, a person of ordinary skill in the relevant art will appreciate that both sensors may be a single structural sensor configured to sense the surrounding environment information of the user and the bioinformation of the user wearing the electronic device 10.

Figure 8:
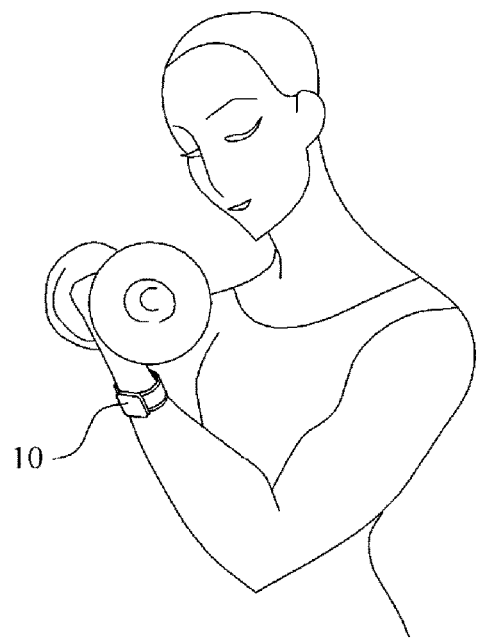
FIG. 8 illustrates an example of an operating method of the electronic device of FIG. 1 based on a state of the user, in accordance with an embodiment.

FIG. 8 illustrates an example of an operating method of the electronic device 10 of FIG. 1 based on a state of a user, in accordance with an embodiment.

Referring to FIG. 8, the electronic device 10 may be worn around a wrist of a user.

The first sensor 100 senses surrounding environment information of a surrounding environment of the user wearing the electronic device 10. The first sensor 100 outputs the sensed surrounding environment information to the controller 300. For example, the surrounding environment information may include at least one of light information, temperature information, noise information, force information, and motion information.

The second sensor 200 senses bioinformation of the user wearing the electronic device 10. The second sensor 200 outputs the bioinformation to the controller 300. For example, the bioinformation includes at least one of biosignal information and biosignal measurement information.

The controller 300 determines an exercising state of the user based on the surrounding environment information and the bioinformation, and controls a change in a function of the electronic device 10 based on the determined exercising state of the user.

The controller 300 changes an internal environment function, for example, an internal function setting, of the electronic device 10 or may change or execute various applications in the electronic device 10 based on the exercising state of the user.

In one illustrative example, the controller 300 controls a deformation in a form of the wearable region 70 used to enable the electronic device 10 to be securely and effectively worn on a portion of a body of the user. The controller 300 controls the wearable region 70 to be further tightened on the portion of the body of the user in which the wearable region 70 is worn to ensure that the electronic device 10 does not fall off the user and is able to effectively receive, process, and monitor biosignals of the user. The controller 300 enables the wearable region 70 to be in closer contact with the user's skin. In addition, the controller 300 changes or executes a function or an application corresponding to recording an exercising time, monitoring heart rates, measuring an EMG, selecting music, coaching an exercise, and/or a ringtone or vibration mode.

Figure 9:
FIG. 9 illustrates another example of an operating method of the electronic device of FIG. 1 based on a state of the user, in accordance with an embodiment.

FIG. 9 illustrates another example of an operating method of the electronic device 10 of FIG. 1 based on a state of a user, in accordance with an embodiment.

Referring to FIG. 9, the electronic device 10 may be worn around a wrist of a user.

The first sensor 100 may generate surrounding environment information on an surrounding environment of the user wearing the electronic device 10. The first sensor 100 outputs the surrounding environment information to the controller 300. For example, the surrounding environment information includes at least one of light information, temperature information, noise information, force information, and motion information.

The second sensor 200 senses bioinformation of the user wearing the electronic device 10. For example, the bioinformation includes bio-reaction information of the user wearing the electronic device 10. For example, the bio-reaction information includes a pulse wave, a skin temperature, a brainwave, a facial muscle movement, and a face temperature. The second sensor 200 outputs the bio-reaction information to the controller 300.

The controller 300 determines a stable state of the user, for example, a sleeping state and a resting state, based on the surrounding environment information and the bioinformation, and controls a deformation in a form of the electronic device 10 based on the determined stable state of the user.

The controller 300 changes an internal environment function, for example, an internal function setting, of the electronic device 10 changes or executes various applications in the electronic device 10 based on the stable state of the user.

In one example, the controller 300 controls a deformation in a form of the wearable region 70 used to allow the electronic device 10 to be worn on a portion of a body of the user. The controller 300 controls the wearable region 70 to be further loosened. In addition, the control processor 330 of the controller 300 changes or executes a function or an application corresponding to recording a stable time, for example, a resting time or a sleeping time, monitoring SpO2, saving power of the electronic device 10, selecting music, and/or a ringtone or vibration mode.

Figure 10:
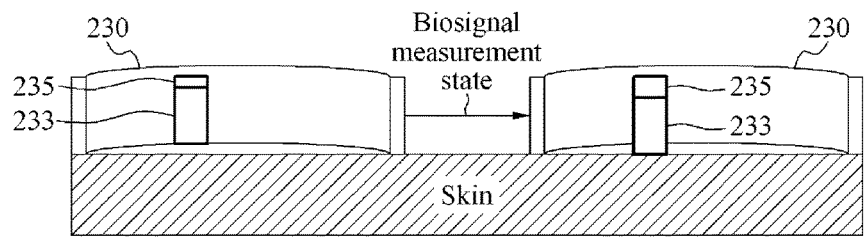
FIG. 10 illustrates still another example of an operating method of the electronic device of FIG. 1 based on a state of the user, in accordance with an embodiment.

FIG. 10 illustrates still another example of an operating method of the electronic device 10 of FIG. 1 based on a state of a user, in accordance with an embodiment.

Referring to FIG. 10, the first sensor 100 generates surrounding environment information of the surrounding environment of the user wearing the electronic device 10. The first sensor 100 outputs the surrounding environment information to the controller 300.

A sensor, for example, the second sensor 200 or the third sensor 400, senses the user wearing the electronic device 10.

In an example, the second sensor 200 senses bioinformation from the user wearing the electronic device 10. The bioinformation includes at least one of biosignal information and biosignal measurement information. The biosignal measurement information may include an input from the user wearing the electronic device 10 requesting a measurement of a biosignal.

In another example, the third sensor 400 senses an input from the user requesting a measurement of a biosignal. The third sensor 400 generates a sensing signal in response to the input from the user. The input from the user is an input to initiate measuring of the biosignal.

The controller 300 determines a state of the user wearing the electronic device 10 based on a result of the sensing output from the sensor, for example, the second sensor 200 or the third sensor 400, and controls a deformation of the wearable region 70 of the electronic device 10 based on the determined state of the user. In an example, the controller 300 determines a biosignal measurement state of the user based on the surrounding environment information and the bioinformation output from the second sensor 200, and controls a deformation of the wearable region 70 of the electronic device 10 based on the biosignal measurement state of the user. In another example, the controller 300 determines the biosignal measurement state of the user in response to the sensing signal output from the third sensor 400, and controls a deformation of the electronic device 10 based on the biosignal measurement state of the user.

The controller 300 may change an internal environment function, for example, an internal function setting, of the electronic device 10 or change or execute various applications in the electronic device 10 based on the biosignal measurement state of the user.

In one illustrative example, the controller 300 controls a deformation of an electrode included in the second sensor 200 to allow the electrode to be in closer contact with the user's skin.

Referring to FIG. 10, the second sensor 200 includes an electrode 233 and an electroactive polymer (EAP) 235. The electrode 233 is an electrode used to sense a biosignal from the user wearing the electronic device 10. The controller 300 controls a deformation to allow the electrode 233 to be in closer contact with skin through the EAP 235. In addition, the control processor 330 of the controller 300 changes or execute a function or an application corresponding to recording a biosignal measurement state, a measurement result, measuring another biosignal, selecting music, a warning, and/or a ringtone or vibration mode.

Figure 11:
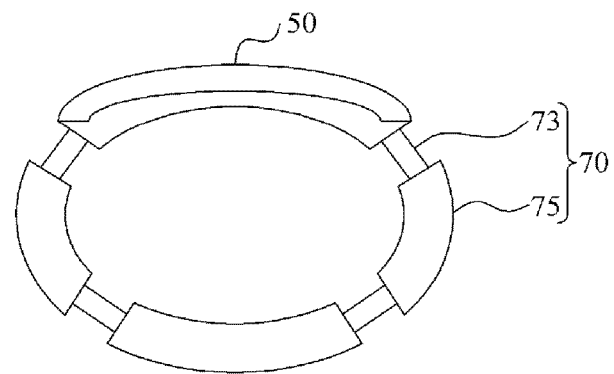
FIG. 11 is a diagram illustrating an example of a deformation of a wearable region as illustrated in FIG. 1, in accordance with an embodiment.

FIG. 11 is a diagram illustrating an example of a deformation of the wearable region 70 illustrated in FIG. 1, in accordance with an embodiment.

Referring to FIGS. 1 through 11, the wearable region 70 includes at least one length adjusting member 73 and at least one supporting member 75.

The length adjusting member 73 connects a main body 50 to the supporting member 75. In addition, the length adjusting member 73 connects the supporting member 75 together.

Based on a control by the controller 300 in the main body 50, a length, a tension, and an elasticity of the length adjusting member 73 may be changed. The length adjusting member 73 is provided in a form of a wire, a string, an elastic body, a cable, a band, a rope, or a strap. The material of the length adjusting member 73 may be any rigid or flexible material such as plastic, resin, metal, aluminum, or polyurethane material.

The supporting member 75 supports onto a portion of a body of a user to allow the electronic device 10 to be worn on the portion of the body of the user.

The controller 300 controls a deformation in a form of the wearable region 70, for example, the length adjusting member 73, to allow the electronic device 10 to be worn on the portion of the body of the user. For example, the length, the tension, or the elasticity of the length adjusting member 73 is changed based on the control by the controller 300. Further, the shape of the length adjusting member 73 may change based on the control by the controller 300.

As described with reference to FIG. 8, when the user is determined to be currently exercising, the controller 300 controls a change in the length, the tension, the shape, or the elasticity of the length adjusting member 73 to tighten the wearable region 70.

As described with reference to FIG. 9, when the user is determined to be currently resting, the controller 300 controls a change in the length, the tension, the shape, or the elasticity of the length adjusting member 73 to loosen the wearable region 70.

Although the example of FIG. 11 illustrates that a circumferential length of the wearable region 70 may be controlled to change through the length adjusting member 73, a change in a function of tightening or loosening the wearable region 70 may be controlled through air injection.

For ease of description, cases of an exercising state, a stable state, for example, a stressful state or a sleeping state, and a biosignal measurement state of the user are illustrated. However, embodiments may be expanded to various states or situations in which the user may be placed.

Figure 12:
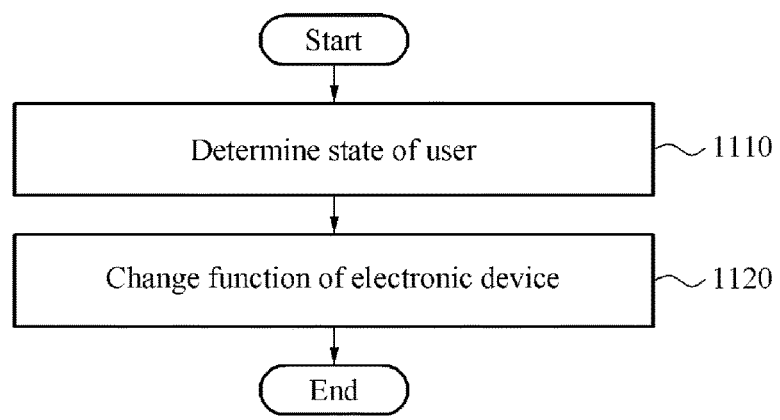
FIG. 12 is a flowchart illustrating an example of an operating method of the electronic device of FIG. 1, in accordance with an embodiment.

FIG. 12 is a flowchart illustrating an example of an operating method of the electronic device 10 of FIG. 1, in accordance with an embodiment.

Referring to FIG. 12, in operation 1110, the electronic device 10 determines a state of a user wearing the electronic device 10 by sensing the user.

In operation 1120, the electronic device 10 controls a change in a function of the electronic device 10 based on the determined state of the user.

Figure 13:
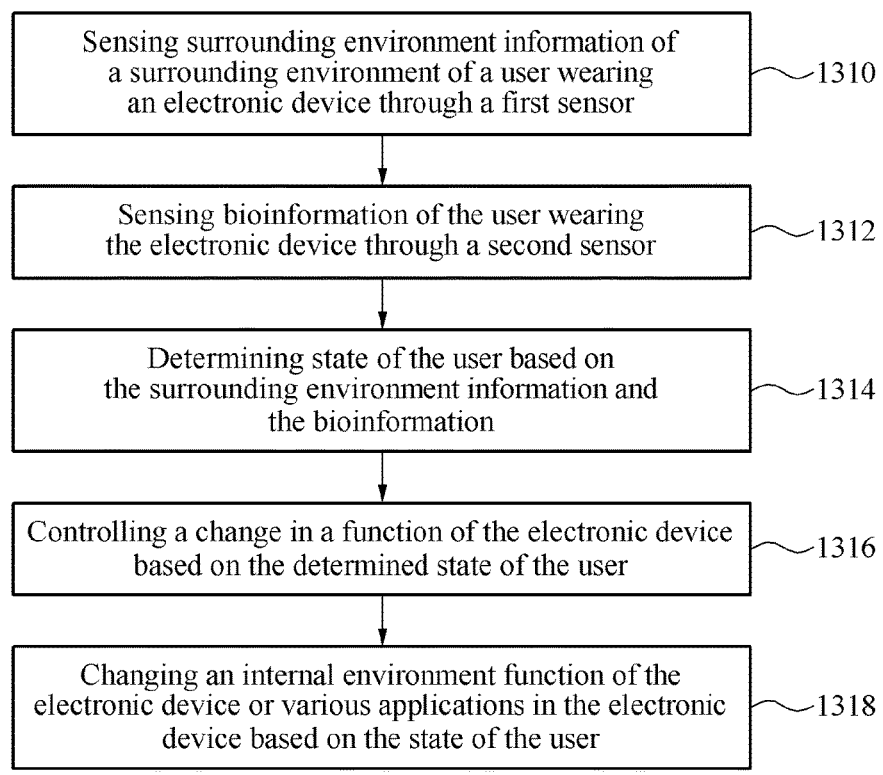
FIG. 13 is a flowchart illustrating an example of a method of the electronic device worn on a wrist, in accordance with an embodiment.

FIG. 13 is a flowchart illustrating an example of a method of the electronic device 10 worn on a wrist, in accordance with an embodiment.

In operation 1310, the method senses surrounding environment information of a surrounding environment of the user wearing the electronic device 10 through a first sensor 100.

In operation 1312, the method senses bioinformation of the user wearing the electronic device 10 through a second sensor 200.

In operation 1314, the surrounding environment information and the bioinformation are received at the controller 300 and state of the user is determined, such as an exercising state or a resting state, based on the surrounding environment information and the bioinformation.

In operation 1316, a change in a function of the electronic device 10 is controlled at the controller 300 based on the determined state of the user.

In operation 1318, an internal environment function, for example, an internal function setting, of the electronic device 10 is changed using the controller 300 or various applications in the electronic device 10 are changed or executed at the controller 300 based on the state of the user. In one illustrative example, the method in the controller 300 controls the deformation in a form of the wearable region 70 used to enable the electronic device 10 to be securely and effectively worn on a portion of the body of the user. The method in the controller 300 controls the wearable region 70 to be further tightened onto the portion of the body of the user in which the wearable region 70 is worn to ensure that the electronic device 10 does not fall off the user and is able to effectively receive, process, and monitor biosignals of the user. In addition, the method in the controller 300 changes or executes a function or an application corresponding to recording an exercising time, monitoring heart rates, measuring an EMG, selecting music, coaching an exercise, and/or a ringtone or vibration mode.

Figure 14:
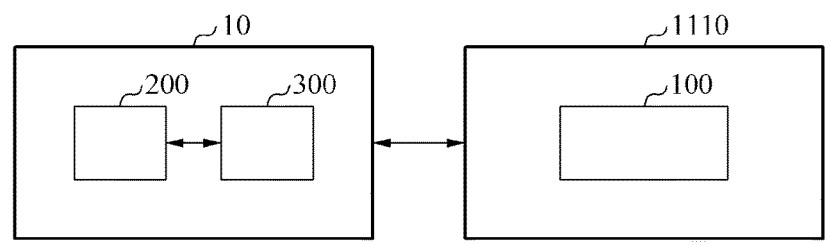
FIG. 14 is a diagram illustrating an example of an electronic system including the electronic device of FIG. 1, in accordance with an embodiment.

FIG. 14 is a diagram illustrating an example of an electronic system 1100 including the electronic device 10 of FIG. 1, in accordance with an embodiment.

Referring to FIG. 13, the electronic system 1100 includes the electronic device 10 and another electronic device 1110.

The electronic device 1110 is configured as a personal computer (PC), a data server, or a portable device.

The portable device includes a laptop computer, a mobile phone, a smartphone, a tablet PC, an MID, a PDA, an EDA, a digital still camera, a digital video camera, a PMP, a PND, a handheld game console, an e-book, or a smart device.

The smart device is provided in a form of a smart watch or a smart band.

For example, the electronic device 1110 is a wearable device to be worn on a user or suitable for being worn.

The electronic device 10 and the electronic device 1110 communicate with each other. The first sensor 100 is configured to generate surrounding environment information and is included in the electronic device 1110. The electronic device 1110 transmits the surrounding environment information to the electronic device 10.

For example, in a case of the electronic device 1110 is a mobile phone or a smartphone, the electronic device 1110 may transmit the surrounding environment information including call information to the electronic device 10. For example, although the call information may be obtained through the first sensor 100, the call information may be directly obtained through the electronic device 1110.

The controller 300 of the electronic device 10 determines a state of the user based on the surrounding environment information transmitted from the electronic device 1110 and bioinformation generated by the second sensor 200, and controls a change in a function of the electronic device 10. For example, the state of the user includes an exercising state, a resting state, a movie watching state, a stressful state, a reading state, a call state, a drowsy driving state, and other various states or situations in which the user may be placed.

Configurations and operations of the first sensor 100, the second sensor 200, and the controller 300 illustrated in FIG. 14 may be substantially identical to those of the first sensor 100, the second sensor 200, and the controller 300 illustrated in FIGS. 2 and 3.

Figure 15:
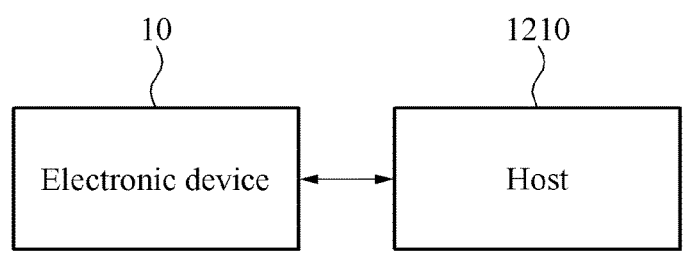
FIG. 15 is a diagram illustrating another example of an electronic system including the electronic device of FIG. 1, in accordance with an embodiment.

FIG. 15 is a diagram illustrating another example of an electronic system 1200 including the electronic device 10 of FIG. 1.

Referring to FIG. 14, the electronic system 1200 includes the electronic device 10 and a host 1210.

In addition to the description provided with reference to FIG. 1, the electronic device 10 may be a patient monitor, an ECG device, a respiratory rate sensor, a pulse rate sensor, a body temperature sensor, an electric conduction sensor, or a medical imaging device.

The electronic device 10 and host 1210 communicates with each other. For example, the electronic device 10 and host 1210 interwork with each other. The electronic device 10 controls the host 1210, or the host 1210 controls the electronic device 10.

The host 1210 is provided in a form of a portable electronic device. The portable electronic device includes a laptop computer, a mobile phone, a smartphone, a tablet PC, an MID, a PDA, an EDA, a digital still camera, a digital video camera, a PMP, a PND, a handheld game console, an e-book, or a smart device.

The smart device is provided in a form of a smart watch or a smart band.

The host 1210 continuously monitors a state of a user wearing the electronic device 10. For example, the state of the user is a health state, a physiological condition, or a medical state.

Figure 16:
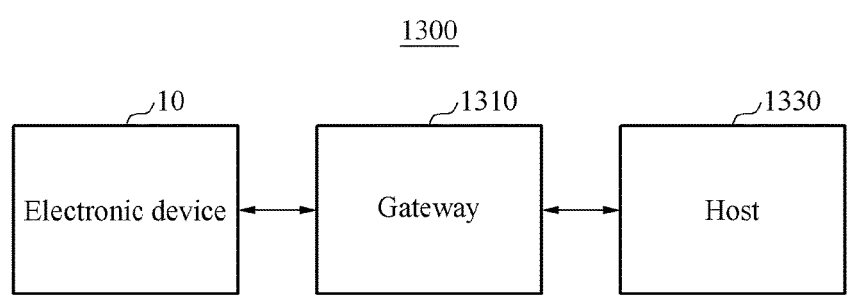
FIG. 16 is a diagram illustrating still another example of an electronic system including the electronic device of FIG. 1, in accordance with an embodiment.

FIG. 16 is a diagram illustrating still another example of an electronic system 1300 including the electronic device 10 of FIG. 1, in accordance with an embodiment.

Referring to FIG. 15, the electronic system 1600 includes the electronic device 10, a gateway 1610, and a host 1630. The electronic system 1600 may be a health monitoring system.

The electronic device 10 and the host 1330 may communicate with each other through the gateway 1310.

The gateway 1610 is provided in a form of a portable electronic device. The portable electronic device includes a laptop computer, a mobile phone, a smartphone, a tablet PC, an MID, a PDA, an EDA, a digital still camera, a digital video camera, a PMP, a PND, a handheld game console, an e-book, or a smart device.

The host 1630 is a medical system of a medical institution.

The apparatuses, processors, modules, devices, and other components illustrated in FIGS. 1-11 and 14-16 that perform the operations described herein with respect to FIGS. 12-13 are implemented by hardware components. Examples of hardware components include controllers, sensors, generators, drivers, and any other electronic components known to one of ordinary skill in the art. In one example, the hardware components are implemented by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 12-13. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 12-13 that perform the operations described herein with respect to FIGS. 1-11 and 14-16 are performed by a processor or a computer as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An electronic device, comprising:
   a biosensor configured to sense bioinformation on a body of a user wearing the electronic device; and
   a controller configured to determine a state of the user by implementing a classifier which considers the bioinformation and sensed surrounding environment information of a surrounding environment of the user, and configured to control a change in a deformation function of the electronic device based on the determined state of the user,
   wherein the controller is configured to perform the determining of the state of the user based on a vector result of the implementation of the classifier, the vector result being dependent on feedback information on a previous change in the deformation function of the electronic device, and
   wherein the classifier indicates a position corresponding to the vector result comprising the numerical value included in the bioinformation and the sensed surrounding environment information.

2. The electronic device of claim 1, wherein the controller is configured to determine the state of the user based on the surrounding environment information and at least one of biosignal information and biosignal measurement information comprised in the bioinformation.

3. The electronic device of claim 2, wherein the biosignal measurement information comprises an input request from the user to measure a biosignal of the user.

4. The electronic device of claim 1, wherein the controller is configured to determine an exercising state of the user based on the bioinformation and motion information comprised in the surrounding environment information and control the change in the deformation function of the electronic device based on the determined exercising state of the user.

5. The electronic device of claim 1, wherein the controller is configured to determine a stable state of the user based on the surrounding environment information and bio-reaction information comprised in the bioinformation and control the change in the deformation function of the electronic device based on the determined stable state of the user.

6. The electronic device of claim 1, wherein the controller is configured to determine a biosignal measurement state of the user based on the surrounding environment information and biosignal measurement information comprised in the bioinformation and control the change in the deformation function of the electronic device based on the determined biosignal measurement state of the user.

7. The electronic device of claim 1, further comprising:
   an environmental sensor configured to sense the surrounding environment information.

8. The electronic device of claim 1, wherein the surrounding environment information is received from another electronic device communicating with the electronic device.

9. The electronic device of claim 1, wherein the biosensor is configured to generate a sensing signal in response to an input from the user, and
the controller is configured to determine the state of the user in response to the sensing signal, and control the change in the deformation function of the electronic device based on the determined state of the user.

10. The electronic device of claim 9, wherein the state of the user is a biosignal measurement state of the user.

11. The electronic device of claim 1, wherein the controller is configured to:
control a deformation function of a region of the electronic device worn on a portion of a body of the user;
control an executing of a function or an application corresponding to monitoring and recording at least one of an exercise time, a heart rate, and an electromyogram (EMG), selecting a music, and selecting a ringtone or a vibration mode, based on the determined state of the user; and
control an executing of a function or an application corresponding to coaching an exercise for the user, based on the determined state of the user.

12. The electronic device of claim 1, wherein the controller is configured to control the deformation function using an electrode comprised in the biosensor.

13. The electronic device of claim 12, wherein the controller is configured to control the deformation function using the electrode through an electroactive polymer (EAP).

14. The electronic device of claim 1, wherein the controller further comprises:
a trainer configured to collect feedback information on the change in the deformation function of the electronic device, and train the classifier based on the feedback information, the surrounding environment information, and the bioinformation.

15. A method of an electronic device, comprising:
sensing bioinformation from a user wearing the electronic device;
determining a state of the user by implementing a classifier which considers the bioinformation and sensed surrounding environment information of a surrounding environment of the user;
controlling a deformation function of the electronic device based on the determined state of the user; and
performing the determining of the state of the user based on a vector result of the implementation of the classifier, the vector result being dependent on feedback information on the deformation function of the electronic device,
wherein the classifier indicates a position corresponding to the vector result comprising the numerical value included in the bioinformation and the sensed surrounding environment information.

16. The method of claim 15, wherein the determining comprises:
determining the state of the user based on the output of the classifier using the surrounding environment information and at least one of biosignal information and biosignal measurement information comprised in the bioinformation.

17. The method of claim 16, wherein the biosignal measurement information comprises an input request from the user to measure a biosignal of the user.

18. The method of claim 15, further comprising:
sensing the surrounding environment information.

19. The method of claim 15, wherein the surrounding environment information is received from another electronic device communicating with the electronic device.

20. The method of claim 15, wherein the determining comprises:
determining an exercising state of the user based on the bioinformation and motion information comprised in the surrounding environment information.

21. The method of claim 15, wherein the determining comprises:
determining a stable state of the user based on the surrounding environment information and bio-reaction information comprised in the bioinformation.

22. The method of claim 15, wherein the determining comprises:
determining a biosignal measurement state of the user based on the surrounding environment information and biosignal measurement information comprised in the bioinformation.

23. The method of claim 15, wherein the controlling comprises:
controlling a deformation of a region of the electronic device to be worn on a portion of a body of the user;
controlling an executing of a function or an application corresponding to monitoring and recording at least one of an exercise time, a heart rate, and an electromyogram (EMG), selecting a music, and selecting a ringtone or a vibration mode, based on the state of the user; and
controlling an executing of a function or an application corresponding to coaching an exercise for the user, based on the state of the user.

24. The method of claim 15, wherein the controlling comprises:
controlling the deformation function using an electrode comprised in a sensor configured to sense the bioinformation.

25. The method of claim 24, wherein the electrode is deformed through an electroactive polymer (EAP).

26. The method of claim 15, further comprising:
collecting the feedback information on the controlled deformation function of the electronic device; and
training the classifier based on the collected feedback information, the surrounding environment information, and the bioinformation.

27. An apparatus, comprising:
a sensor configured to sense bioinformation and information of a surrounding environment of a user wearing an electronic device; and
a controller configured to determine a state of the user by implementing a classifier which considers the bioinformation and the surrounding environment information, and configured to control a deformation function of a wearable region of the electronic device based on the determined state of the user,
wherein the controller is configured to perform the determining of the state of the user based on a vector result of the implementation of the classifier, the vector result being dependent on feedback information on the deformation function of the electronic device, and
wherein the classifier indicates a position corresponding to the vector result comprising the numerical value included in the bioinformation and the sensed surrounding environment information.

28. The apparatus of claim 27, wherein the surrounding environment information comprises at least one of light information, temperature information, noise information, force information, and motion information.

29. The apparatus of claim 27, wherein the bioinformation comprises at least one of a pulse wave, a skin temperature, a brainwave, a facial muscle movement, and a face temperature.

30. The apparatus of claim 27, wherein the determiner is further configured to determine the state as an exercising state or a stable state of the user through the classifier based on the bioinformation and motion information included in the surrounding environment information, and wherein the controller comprises a trainer configured to collect the feedback information on the deformation function of the electronic device, and train the classifier based on the collected feedback information, the surrounding environment information, and the bioinformation.

31. The apparatus of claim 30, wherein the determiner is configured to produce data included in the surrounding environment information and the bioinformation as an input vector comprising a numerical value of the each data, and use personal information of the user to adjust the state of the user wearing the electronic device, wherein the determiner is further configured to provide the input vector to the classifier, and wherein the data comprises acceleration data, coordinate data, and heart rate data, and the personal information comprises an age, a height, and a weight of the user.

32. The apparatus of claim 30, wherein, in response to the determiner determining that the state of the user is a stable state comprising a sleeping state or a resting state, the controller controls the deformation function of the wearable region worn on a portion of a body of the user by loosening the wearable region.

33. The apparatus of claim 32, wherein the controller executes a function or an application to monitor and record at least one of a resting time and a sleeping time, a saturation level of partial pressure oxygen ($SpO_2$), an amount of power saving of the electronic device, select a music, and select a ringtone or a vibration mode.

34. The apparatus of claim 30, wherein, in response to the determiner determining that the state of the user is an exercise state, the controller controls the deformation function of the wearable region worn on a portion of a body of the user by tightening the wearable region.

35. The apparatus of claim 34, wherein the controller executes a function or an application corresponding to monitoring and recording at least one of an exercise time, a heart rate, and an electromyogram (EMG), selecting a music, and selecting a ringtone or a vibration mode, and wherein the controller executes a function or an application corresponding to coaching an exercise for the user.

36. The apparatus of claim 30, wherein, in response to the determiner determining that the user is measuring a biosignal, the controller controls the deformation function to enable an electrode included in the sensor to be in close contact with skin of the user.

* * * * *